United States Patent [19]

Reiss

[11] 4,288,344

[45] Sep. 8, 1981

[54] STABLE DIAZONIUM SALT GENERATOR FOR IMPROVED MARIJUANA ANALYSIS

[76] Inventor: Andre Reiss, 147-47 Village Rd., Jamaica, N.Y. 11435

[21] Appl. No.: 55,616

[22] Filed: Jul. 9, 1979

Related U.S. Application Data

[63] Continuation-in-part of Ser. No. 744,288, Nov. 22, 1976, abandoned, and Ser. No. 903,750, May 8, 1978, abandoned.

[51] Int. Cl.³ .................... G01N 21/06; G01N 31/22; C09K 3/00
[52] U.S. Cl. .............................. 252/408; 23/230 R; 23/230 B; 23/230 M; 23/910; 260/141
[58] Field of Search .......... 252/408; 23/230 R, 230 B, 23/230 M, 910; 260/141, 152, 207, 207.1, 208

[56] References Cited

U.S. PATENT DOCUMENTS

| | | | |
|---|---|---|---|
| 3,415,717 | 12/1968 | Avakian | 252/408 |
| 3,511,607 | 5/1970 | Green | 252/408 |
| 3,585,001 | 6/1971 | Mast | 252/408 |
| 3,585,004 | 6/1971 | Mast | 252/408 |
| 3,814,586 | 6/1974 | Fraser, Jr. et al. | 252/408 |
| 3,817,705 | 6/1974 | Stein et al. | 252/408 |
| 3,850,576 | 11/1974 | Rittersdorf et al. | 23/230 B |
| 3,955,926 | 5/1976 | Fischer | 252/408 |
| 4,029,598 | 6/1977 | Neisius et al. | 252/408 |
| 4,172,049 | 10/1979 | Pfeil et al. | 252/408 |
| 4,190,419 | 2/1980 | Bauer | 23/230 B |

OTHER PUBLICATIONS

"Zirconium oxychloride", The Condensed Chemical Dictionary, 8th Ed., Hawley, G. G., Van Nostrand Reinhold Co., N.Y., p. 956 (1971).
The Merck Index, 8th Ed., Stecher, P. G., et al., Merck & Co., Inc., Rahway, N.J., pp. 957, 1132 & 1133 (1968).
Irgdayasamy, A., et al., Indian J. Chem., vol. 3, pp. 327-328 (1965).
C.A., vol. 85, 154660g (1976).
De Faubert Maunder, M. J., J. Assoc. Publ. Anal., vol. 7, No. 1, pp. 24-30 (1969).
De Faubert Maunder, M. J., Bulletin on Narcotics, vol. XXVI, No. 4, pp. 19-26 (Oct.-Dec. 1974).
C.A., vol. 83, 23043u (1975).
C.A., vol. 71, 110978y (1969).
C.A., vol. 71, 33466a (1969).

*Primary Examiner*—Teddy S. Gron

[57] ABSTRACT

A stable, two liquid reagent set for detecting Marijuana is described. The two liquids contain a coupling reagent for Marijuana Phenols and a second color developing reagent. Marijuana plant Phenols successively treated with one drop each of these solutions will produce a characteristic red dye. The compositions remain stable over six months.

2 Claims, No Drawings

STABLE DIAZONIUM SALT GENERATOR FOR IMPROVED MARIJUANA ANALYSIS

BACKGROUND OF THE INVENTION

This is a continuation-in-part of application Ser. Nos. 744,288 and 903,750 filed respectively Nov. 22, 1976 and May 8, 1978 under the title: 'Stable Diazonium Salt Generator for Improved Marijuana Analysis,' and now abandoned.

The present invention relates to a diazotizing Composition of Matter to provide a newly stable reagent for Marijuana detection.

Historically, Diazonium Salts have proven valuable as analytical reagents and dyestuff components. However, their instability in liquid form has proven a serious liability. With a life span of only days before decomposing, pre-packaged solutions of Diazonium Salts have not been commercialized. Alternative mixtures of the dry Salts with an inert material, to be dissolved just before use, have been found too cumbersome.

Therefore, dry Salt mixtures of Fast Blue BB Salt, an excellent reagent for the detection of Marijuana, have not been widely used in pre-packaged test kits. More stable though less reliable methods have had to be substituted.

The primary objective of this invention has been to provide a stable liquid composition Fast Blue BB Salt, able to detect Marijuana reliably in pre-packaged test kit form. Another objective has been to provide a Composition of Matter wherein another Diazonium Salt may replace Fast Blue BB Salt, thereby preparing for future stable liquid reagents requiring unstable Diazonium Salts.

BRIEF SUMMARY OF THE INVENTION

Instead of attempting to keep Diazonium Salt solutions stable, proven unsuccessful in over 50 years of attempts, this invention introduces a unique diazotizing composition, able to diazotize precursor Amines to their corresponding Diazonium Salts "in situ."

The diazotizing medium of the invention comprises Zirconium Oxychloride and Sodium Cobaltinitrite dissolved in Methyl Cellosolve. Such diazotizable Amine, Fast Blue BB Base herein applied for Marijuana detection, is also dissolved in the solution so that added water will catalyze generation of the Amine's corresponding Salt, Fast Blue BB Salt. The generated Diazonium Salt may then react with a suitable Phenol under preferably aqueous alkaline conditions to provide a characteristic dye color identifying that Phenol; i.e. Marijuana plant Phenols forming a reddish dyestuff.

The unstable Diazonium Salt is thus produced "in situ" from a stable diazotizing Composition of Matter as an alternative to storing the unstable Salt in solution. Moreover, a stable colorimetric spot test for the detection of Marijuana Phenols, requiring but two liquid reagents, is hereby made possible.

DETAILED DESCRIPTION OF THE INVENTION

This invention is best described as a Diazonium Salt Generator, able to hold in stable solution a diazotizable Amine and diazotize such Amine to its corresponding Diazonium Salt on addition of water. At the Generator's heart lies the discovery that a solution of Zirconium Oxychloride ($ZrOCl_2.8H_2O$) in Methyl Cellosolve (Ethylene Glycol Monomethyl Ether, $CH_3OCH_2CH_2OH$) exerts an unexpectedly strong chelating action, permitting both solubilization and stable co-existence of the diazotizable Amine Fast Blue BB Base (4-Benzoylamino-2,5 diethoxyaniline) with Sodium Cobaltinitrite ($Na_3Co(NO_2)_6$.)

A general composition for the Diazonium Salt Generator requires Methyl Cellosolve be saturated with both Zirconium Oxychloride and Sodium Cobaltinitrite. Specific preparation and use details are as follows.

Marijuana detection with a pre-packaged kit requires two liquids: a Diazonium Salt generating reagent and an aqueous alkaline developer. The diazotizing reagent comprises 35 g Zirconium Oxychloride dissolved in one liter Methyl Cellosolve, to which 2 g Fast Blue BB Base are then dissolved. The solution is chilled to 1°-3° C. after which 4 g Sodium Cobaltinitrite are dissolved. The finished solution may be stored at room temperature. The second developer solution comprises 30 g Sodium Carbonate dissolved in one liter water.

Approximately 10 milligrams of plant substance are placed on white paper or cloth, then successively covered by one drop each of the diazotizing and developer reagents described. If the plant material is truly Marijuana, coupling of the generated Diazonium Salt with plant Phenols will produce a red dye. The reagents remain effective over six months.

Simplicity of only two liquid reagents for Marijuana detection, versatility of Diazonium Salt substitution, and the inherent stability created through generation, not storage, of the required Diazonium Salt, all arise from the unique usefulness of this Diazonium Salt Generator. Therefore, while the invention has been described by means of a specific example and in a specific embodiment, I do not wish to be limited thereto, for obvious modifications will occur to those skilled in the art without departing from the spirit and scope of the invention.

I claim:

1. A Composition of Matter utilized as a Diazonium Salt Generator comprising Methyl Cellosolve, saturated with Zirconium Oxychloride and Sodium Cobaltinitrite.

2. A Composition of Matter used as a reagent in a pre-packaged test kit for Marijuana detection comprising Fast Blue BB Base dissolved in a diazotizing solution of Methyl Cellosolve saturated with Zirconium Oxychloride and Sodium Cobaltinitrite; contact of said reagent with Marijuana plant Phenols producing a characteristic reddish dye color when developed by an equal volume of a second aqueous alkaline solution.

* * * * *